United States Patent

Cotteret et al.

[11] Patent Number: 5,683,474
[45] Date of Patent: *Nov. 4, 1997

[54] METHOD FOR DYEING KERATINOUS FIBRES USING 4-HYDROXYINDOLE DERIVATIVES AT ACID PH AND COMPOSITIONS USED

[75] Inventors: Jean Cotteret, Verneuil-sur-Seine; Marie Pascale Audousset, Levallois-Perret, both of France

[73] Assignee: L'Oreal, Paris, France

[*] Notice: The term of this patent shall not extend beyond the expiration date of Pat. No. 5,609,649.

[21] Appl. No.: 461,845

[22] Filed: Jun. 5, 1995

Related U.S. Application Data

[63] Continuation of Ser. No. 71,349, Jun. 3, 1993, abandoned, which is a continuation of Ser. No. 725,069, Jul. 5, 1991, abandoned.

[30] Foreign Application Priority Data

Jul. 5, 1990 [FR] France ................. 90 08570

[51] Int. Cl.$^6$ ................. A61K 7/13
[52] U.S. Cl. ................. 8/409; 8/407; 8/408; 8/410; 8/411; 8/412; 8/423
[58] Field of Search ................. 8/406, 407, 408, 8/409, 410, 411, 412, 423

[56] References Cited

U.S. PATENT DOCUMENTS

| 5,034,015 | 7/1991 | Junino et al. | 8/405 |
|---|---|---|---|
| 5,131,911 | 7/1992 | Lang et al. | 8/405 |
| 5,391,206 | 2/1995 | Cotteret | 8/409 |

FOREIGN PATENT DOCUMENTS

| 428441 | 5/1991 | European Pat. Off. . | |
| 2 636 237 | 3/1990 | France . | |
| 3 441 148 | 5/1986 | Germany . | |
| 2 211 517 | 7/1989 | United Kingdom . | |

OTHER PUBLICATIONS

English language translation of DE 3,031,709, Wella AG, published Apr. 22, 1982, pp. 1–12.

*Primary Examiner*—Paul Lieberman
*Assistant Examiner*—Caroline L. Dusheck
*Attorney, Agent, or Firm*—Jacobson, Price, Holman & Stern, PLLC

[57] ABSTRACT

Method for dyeing keratinous fibres, in particular human keratinous fibres such as hair, characterized in that a composition containing, in a medium appropriate for dyeing, at least one 4-hydroxyindole derivative of formula:

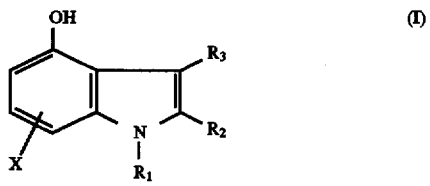

in which $R_1$ denotes hydrogen or $C_1$–$C_4$ alkyl; $R_2$ and $R_3$, which may be identical or different, denote hydrogen, $C_1$–$C_4$ alkyl, carboxyl or alkoxycarbonyl; and X denotes hydrogen, $C_1$–$C_4$ alkyl, $C_1$–$C_{18}$ alkoxy, halogen or acetyl-amino; at least one of the groups X, $R_1$, $R_2$ and $R_3$ being other than hydrogen; as well as the salts of these compounds;

- at least one oxidation dye precursor; and
- at least one oxidizing agent; is applied to said fibres, the pH of the composition applied to the fibres being less than 7.

23 Claims, No Drawings

METHOD FOR DYEING KERATINOUS FIBRES USING 4-HYDROXYINDOLE DERIVATIVES AT ACID PH AND COMPOSITIONS USED

This is a continuation of application Ser. No. 08/071,349, filed Jun. 3, 1993, abandoned which is a continuation of application Ser. No. 07/725,069, filed Jul. 5, 1991, abandoned.

The present invention relates to a new method for dyeing keratinous fibres, in particular human keratinous fibres, using 4-hydroxyindole derivatives in combination with oxidation bases and an oxidising agent in an acid medium and to the compositions used in the course of this method.

It is known to dye keratinous fibres and in particular human hair using tinctorial compositions containing, in an alkaline medium, oxidation dye precursors and in particular p-phenylenediamines or ortho- or para-aminophenols, generally termed "oxidation bases".

It is also known that the shades obtained with these oxidation bases can be varied by combining said bases with couplers, also termed colour modifiers, chosen, in particular, from aromatic meta-diamines, meta-aminophenols and meta-diphenols.

The Applicant has just discovered that the use of 4-hydroxyindole derivatives in combination with oxidation bases led, when this combination was applied to the hair in the presence of an oxidising agent and at acid pH, to dyeings having an improved tinctorial power. The dyeings thus obtained also have an excellent stability to light, to washing, to perspiration and to the weather.

These results are particularly surprising when they are compared with those obtained with conventional couplers of the benzene series mentioned above, where a loss of tinctorial power and a lower stability is often found when the method is carried out at acid pH.

The present invention therefore relates to a method for dyeing keratinous fibres, in particular human keratinous fibres such as hair, comprising the application to these fibres of at least one composition containing a hydroxyindole compound of formula (I) as defined below, an oxidation dye precursor, also termed oxidation base, and an oxidising agent, at acid pH.

The invention also relates to a two-component agent for dyeing, one of which components comprises the 4-hydroxyindole derivative and the oxidation dye precursor and the other comprises the oxidising agent at an acid pH, and in amounts such that the mixture has an acid pH.

The invention also relates to the ready-to-use composition containing the various agents used for dyeing hair in an acid medium.

Further subjects of the invention will become apparent on reading the description and the examples which follow.

The method for dyeing keratinous fibres and in particular human keratinous fibres such as hair, according to the invention, is essentially characterised in that a composition containing, in a medium appropriate for dyeing, at least one coupler corresponding to the formula:

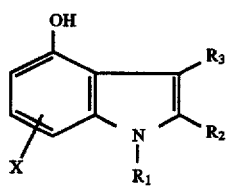

in which $R_1$ denotes a hydrogen atom or a $C_1$–$C_4$ alkyl radical; $R_2$ and $R_3$, which may be identical or different, denote a hydrogen atom, a $C_1$–$C_4$ alkyl radical, a carboxyl radical or an alkoxycarbonyl radical; and X denotes a hydrogen atom, a $C_1$–$C_4$ alkyl radical, a $C_1$–$C_{18}$ alkoxy radical, a halogen atom or an acetylamino group; at least one of the groups X, $R_1$, $R_2$ and $R_3$ being other than hydrogen; as well as the salts of these compounds;

at least one oxidation dye precursor or oxidation base; and at least one oxidising agent; is applied to said fibres, the pH of the composition applied to the fibres being less than 7.

The preferred compounds corresponding to the formula (I), used according to the invention, are the compounds in which the alkyl radical denotes methyl or ethyl and the alkoxycarbonyl radical denotes methoxy-carbonyl or ethoxycarbonyl.

Amongst these compounds, the following may be mentioned: 4-hydroxy-5-ethoxyindole, 4-hydroxy-5-methoxyindole, 4-hydroxy-1-methyl-5-ethoxyindole, 4-hydroxy-2-ethoxycarbonyl-5-ethoxyindole, 4-hydroxy-2-methyl-5-ethoxyindole, 4-hydroxy-7-methoxy-2,3-dimethylindole and 4-hydroxy-5-methylindole.

The salts are chosen more particularly from the hydrochlorides or hydrobromides.

The oxidation dye precursors or oxidation bases are known compounds which are not themselves dyes and which form a dye by means of an oxidative condensation process, either on themselves or in the presence of a coupler or modifier. These compounds generally comprise an aromatic ring carrying functional groups consisting: either of two amino groups; or of an amino group and a hydroxyl group; these groups being in the para- or ortho-position relative to one another.

The oxidation dye precursors of the para type, used according to the invention, are chosen more particularly from para-phenylenediamines, para-aminophenols and para heterocyclic precursors, such as 2,5-diaminopyridine, 2-hydroxy-5-aminopyridine and 2,4,5,6-tetraaminopyrimidine.

Para-phenylenediamines which may be mentioned are the compounds corresponding to the formula (II):

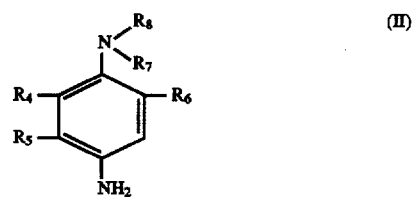

in which $R_4$, $R_5$ and $R_6$, which may be identical or different, represent a hydrogen or halogen atom, an alkyl radical having from 1 to 4 carbon atoms or an alkoxy radical having from 1 to 4 carbon atoms; and $R_7$ and $R_8$, which may be identical or different, represent a hydrogen atom or an alkyl, hydroxyalkyl, alkoxyalkyl, carbamyl-alkyl, mesylaminoalkyl, acetylaminoalkyl, ureidoalkyl, carbalkoxyaminoalkyl, piperidinoalkyl, or morpholinoalkyl radical; these alkyl or alkoxy groups having from 1 to 4 carbon atoms, or $R_7$ and $R_8$ form, together with the nitrogen atom to which they are bonded, a piperidino or morpholino heterocycle, on condition that $R_4$ or $R_5$ represents a hydrogen atom when $R_7$ and $R_8$ do not represent a hydrogen atom, and the salts of these compounds.

Particularly preferred compounds corresponding to the formula (II) which may be mentioned are p-phenylenediamine, 2-methyl-p-phenylenediamine, methoxy-para-phenylenediamine, chloro-paraphenylenediamine, 2,6-dimethyl-para-phenylenediamine, 2,5-dimethyl-para-phenylenediamine, 2,3-dimethyl-para-phenylenediamine, 2-methyl-5-methoxy-para-phenylenediamine, 2,6-dimethyl-5-methoxy-para-phenylenediamine, N,N-dimethyl-para-phenylenediamine, 3-methyl-4-amino-N,N-diethylaniline, N,N-di-(β-hydroxyethyl)para-phenylenediamine, 3-methyl-4-amino-N,N-di-(β-hydroxyethyl)aniline, 3-chloro-4-amino-N,N-di-(β-hydroxyethyl)aniline, 4-amino-N,N-(ethyl, carbamylmethyl)aniline, 3-methyl-4-amino-N,N-(ethyl, carbamylmethyl)aniline, 4-amino-N,N-(ethyl,β-piperidino-ethyl)aniline, 3-methyl-4-amino-N,N-(ethyl,β-piperidino-ethyl)aniline, 4-amino-N,N-(ethyl,β-morpholino-ethyl)aniline, 3-methyl-4-amino-N,N-(ethyl,β-morpholino-ethyl)aniline, 4-amino-N,N-(ethyl,β-acetylaminoethyl)-aniline, 4-amino-N-(β-methoxyethyl)aniline, 3-methyl-4-amino-N, N-(ethyl,β-acetylaminoethyl)aniline, 4-amino-N,N-(ethyl, β-mesylaminoethyl)aniline, 3-methyl-4-amino-N,N-(ethyl, β-mesylaminoethyl)aniline, 4-amino-N,N-(ethyl,β-sulphoethyl)aniline, 3-methyl-4-amino-N,N-(ethyl, β-sulphoethyl)aniline, N-[(4'-amino)phenyl]morpholine and N-[(4'-amino)phenyl]piperidine.

These oxidation dye precursors of the para type may be introduced into the tinctorial composition either in the form of the free base or in the form of salts, such as in the form of the hydrochloride, hydrobromide or sulphate.

p-Aminophenols which may be mentioned are p-aminophenol, 2-methyl-4-aminophenol, 3-methyl-4-aminophenol, 2-chloro-4-aminophenol, 3-chloro-4-aminophenol, 2,6-dimethyl-4-aminophenol, 3,5-dimethyl-4-aminophenol, 2,3-dimethyl-4-aminophenol, 2-hydroxymethyl-4-aminophenol, 2-(β-hydroxyethyl)-4-aminophenol, 2-methoxy-4-aminophenol, 3-methoxy-4-aminophenol, 2,5-dimethyl-4-aminophenol and 2-methoxymethyl-4-aminophenol.

The oxidation dye precursors of the ortho type are chosen from ortho-aminophenols, such as 1-amino-2-hydroxybenzene, 6-methyl-1-hydroxy-2-aminobenzene and 4-methyl-1-amino-2-hydroxybenzene, and ortho-phenylene-diamines.

The oxidising agent is preferably chosen from hydrogen peroxide, urea peroxide, alkali metal bromates and persalts such as perborates and persulphates. Hydrogen peroxide is particularly preferred.

The compositions of the invention do not contain either iodide ions or nitrite ions in an amount sufficient to oxidise the indole derivative of formula (I) and the oxidation dye precursor.

The pH of the composition applied to the keratinous fibres, in particular the hair, has a value of below 7 and is preferably between 3 and 6.9. This pH is adjusted using acidifying agents well known in the field of dyeing of keratinous fibres, and in particular of human hair, such as inorganic acids, such as hydrochloric acid or phosphoric acid, or organic acids, such as carboxylic acids, such as tartric acid or citric acid.

The compounds of formula (I) are present in the composition applied to the keratinous fibres in proportions of preferably between 0.01 and 3.5% by weight relative to the total weight of the composition.

The compositions, defined above, applied in the dyeing of keratinous fibres may also contain, in addition to the heterocyclic couplers of formula (I), other couplers known per se, such as meta-diphenols, meta-aminophenols, meta-phenylenediamines, meta-N-acylaminophenols, meta-ureidophenols, meta-carbalkoxyaminophenols, α-naphthol and couplers containing an active methylene group, such as the diketone compounds and pyrazolones.

Amongst these couplers which may be used in addition to the couplers of formula (I), the following may be mentioned: 2,4-dihydroxyphenoxyethanol, 2,4-dihydroxyanisole, meta-aminophenol, resorcinol, resorcinol monomethyl ether, 2-methylresorcinol, pyrocatechol, 2-methyl-5-N-(β-hydroxyethyl)aminophenol, 2-methyl-5-N-(β-mesylaminoethyl)aminophenol, 6-hydroxy-benzomorpholine, 2,4-diaminoanisole, 2,4-diaminophenoxy-ethanol, 6-aminobenzomorpholine, [2-N-(β-hydroxyethyl)-amino-4-amino]-phenoxyethanol, 2-amino-4-N-(β-hydroxy-ethyl)aminoanisole, (2,4-diamino)phenyl-β,γ-dihydroxy-propyl ether, 2,4-diaminophenoxyethylamine, 1,3-di-methoxy-2,4-diaminobenzene, 2-methyl-5-aminophenol, 2,6-dimethyl-3-aminophenol, 3,4-methylenedioxyphenol and 3,4-methylenedioxyaniline and their salts.

The tinctorial compositions of the invention may also contain direct dyes such as the derivatives of the benzene series, azo dyes, anthraquinone dyes, triphenylmethane and its derivatives, or xanthene or azine dyes. They may also contain rapid oxidation dyes.

These compositions may also contain anionic, cationic, nonionic or amphoteric surface-active agents or their mixtures.

Amongst these surface-active agents, the following may be mentioned: fatty alcohol alkylbenzenesulphonates, alkylnaphthalenesulphonates, sulphates, ether-sulphates and sulphonates, quaternary ammonium salts, such as trimethylcetylammonium bromide, cetylpyridinium bromide, optionally oxyethylenated fatty acid ethanolamides, polyoxyethylenated acids, alcohols or amines, polyglycerolated alcohols, polyoxyethylenated or polyglycerolated alkylphenols and polyoxyethylenated alkyl sulphates.

The tinctorial compositions are generally aqueous but they may also contain organic solvents in order to dissolve compounds which would not be sufficiently soluble in water. Among these solvents, the following may be mentioned as examples: $C_2$–$C_4$ lower alkanols, such as ethanol and isopropanol, glycerol, glycols or glycol ethers, such as 2-butoxyethanol, ethylene glycol, propylene glycol, diethylene glycol monoethyl ether and monomethyl ether, and propylene glycol monoethyl ether and monomethyl ether, and also aromatic alcohols, such as benzyl alcohol or phenoxyethanol, or mixtures of these solvents.

The composition applied to the hair may also contain thickeners chosen in particular from sodium alginate, gum arabic, cellulose derivatives, such as methyl cellulose, hydroxyethyl cellulose, hydroxypropyl cellulose, hydroxymethyl cellulose and carboxymethyl cellulose, optionally crosslinked acrylic acid polymers and xanthan gum. It is also possible to use inorganic thickeners such as bentonite.

The composition may also contain antioxidants, chosen in particular from sodium sulphite, thioglycolic acid, sodium bisulphite, ascorbic acid and hydroquinone, as well as other cosmetically acceptable adjuvants when the composition is intended to be used for dyeing human keratinous fibres, such as penetration agents, sequestering agents, preservatives, buffers, perfumes, and the like.

The composition applied to the hair may be in diverse forms, such as liquids, creams or gels or in any other form appropriate for carrying out hair dyeing. It may be packaged in an aerosol can in the presence of a propellant.

The invention also relates to the ready-to-use composition used in the method defined above.

According to a preferred embodiment, the method comprises a preliminary step consisting in storing separately on the one hand the composition containing, in a medium appropriate for dyeing, the coupler corresponding to the formula (I) defined above and the oxidation dye precursors, in the form of a component (A), and, on the other hand, a composition containing the oxidising agent as defined above, in the form of a component (B), and in preparing a mixture thereof for use before applying this mixture to the keratinous fibres, as indicated above.

The composition applied to the keratinous fibres results from a mixture of 10 to 90% of the component (A) with 90 to 10% of the component (B) containing an oxidising agent.

The invention also relates to an agent for dyeing keratinous fibres, in particular hair, essentially characterised in that it comprises at least two components, one of the components consisting of the component (A) defined above and the other consisting of the component (B), also defined above, the pH of the components (A) and (B) being such that, after mixing in proportions of 90 to 10% in respect of component (A) and of 10 to 90% in respect of component (B), the resulting composition has a pH of less than 7.

The component (A) does not contain either iodide ions or nitrite ions in an amount sufficient to oxidise the indole derivative of formula (I) and the oxidation dye precursor.

In this embodiment the component (A), which contains at least the coupler of formula (I) and an oxidation dye precursor, may have a pH of between 3 and 10.5 and may be adjusted to the chosen value using alkalinising agents customarily used in dyeing keratinous fibres, such as ammonia, alkali metal carbonates or alkanolamines, such as mono-, di- and triethanolamines and their derivatives, or conventional acidifying agents, such as inorganic acids, such as hydrochloric or phosphoric acid, or organic acids, such as carboxylic acids, such as tartric or citric acid.

This composition may contain the various other adjuvants mentioned above, in particular couplers other than the couplers derived from 4-hydroxyindole and corresponding to the formula (I) already mentioned above.

The system comprising oxidation dye precursors of the para and/or ortho type and also the couplers are present in proportions of preferably between 0.05 and 7% by weight relative to the total weight of the component (A). The concentration of compounds of formula (I) may vary between 0.01 and 4% by weight relative to the total weight of the component (A).

The surface-active agents are present in the component (A) in proportions of 0.1 to 55% by weight. If the mixture contains solvents in addition to water, the latter are present in proportions of between 0.5 and 40%. by weight, and in particular of between 5 and 30% by weight, relative to the total weight of the component (A). The thickeners are preferably present in proportions of between 0.1 and 5%, and in particular of between 0.2 and 3%, by weight. The antioxidants mentioned above are preferably present in the component (A) in proportions of between 0.02 and 1.5% by weight relative to the total weight of the component (A).

The component (B) containing the oxidising agent as defined above has a pH of less than 7. This pH may have a minimum value of 1 and it is preferably between 1.5 and 3.5. This component (B) may be acidified using the same type of acidifying agents as those used for the component (A).

It may be in the form of a liquid thickened to a greater or lesser extent or of a milk or gel.

This two-component dyeing agent may be packaged in a multi-compartment device or dyeing kit, or any other multi-compartment packaging system in which one compartment contains the component (A) and the second compartment contains the component (B); these devices may be fitted with means permitting the desired mixture to be delivered onto the hair, such as the devices described in the applicant's U.S. Pat. No. 4,823,985.

The invention also relates to the use of 4-hydroxyindole derivatives corresponding to the formula (I) as a coupler for dyeing keratinous fibres in an acid medium, in combination with oxidation dye precursors.

According to the invention, the dyeing method consists in applying the mixture obtained to the hair, leaving it on the hair for 3 to 40 minutes, then rinsing the hair and optionally shampooing.

It is also possible, according to the invention, separately to apply a composition containing the coupler of formula (I), the oxidation dye precursor and the oxidising agent in such a way that the mixture forming in situ on the fibres has a pH of less than 7, as defined above.

The following examples are intended to illustrate the invention without, however, having a limiting character.

EXAMPLES 1 TO 6

Hair is dyed by applying a mixture, prepared for use, of the dyeing composition (A) and the oxidising composition (B) to grey hair which is 90% white.

This mixture has the pH indicated in the table of examples which follow. This mixture is allowed to act for 30 minutes and the hair is then rinsed and shampooed. After drying, the hair is dyed in the shade specified at the bottom of the table.

| | in g | | |
|---|---|---|---|
| | 1 | 2 | 3 |
| A) Dyeing composition | | | |
| 2,3-dimethyl-7-methoxy-4-hydroxyindole | 0.573 | 0.191 | 0.573 |
| 2,6-dimethyl-para-phenylenediamine.2HCl | 0.657 | | 0.657 |
| Para-phenylenediamine | | 0.324 | |
| Para-aminophenol | 0.327 | | |
| 2-methyl-5-N-(β-hydroxyethyl)-aminophenol | | 0.167 | |
| Monoethanolamine qs pH | 9.2 | 9.9 | 8.9 |
| Carrier 1 | | X | |
| Carrier 2 | X | | X |
| Water qs | 100 | 100 | 100 |
| B) Oxidising composition | | | |
| 20 volume hydrogen peroxide solution | | | |
| Phosphoric acid qs pH | 1.2 | 1.3 | 1.2 |
| pH Of wt/wt A + B mixture | 6.5 | | 6.4 |
| pH of ⅓ A + ⅔ B mixture | | 4.4 | |
| Shades obtained: | iridescent light blond | light ash blond | grey |

| | in g | | |
|---|---|---|---|
| | 4 | 5 | 6 |
| A) Dyeing composition | | | |
| 2,3-dimethyl-7-methoxy-4-hydroxyindole | 0.191 | | |
| 4-hydroxy-5-methoxyindole | | 0.489 | 0.489 |
| 2,6-dimethyl-para-phenylenediamine.2HCl | | 0.657 | |
| Para-phenylenediamine | | | 0.324 |
| 2-methyl-para-phenylenediamine.2HCl | 0.366 | | |
| Meta-aminophenol | 0.109 | | |
| α-naphthol | 0.144 | | |
| Monoethanolamine qs pH | 9.7 | 8.9 | 9.1 |

| -continued | | | |
|---|---|---|---|
| Carrier 1 | X | | |
| Carrier 2 | | X | X |
| Water qs | 100 | 100 | 100 |
| B) Oxidising composition 20 volume hydrogen peroxide solution | | | |
| Phosphoric acid qs pH | 1.3 | 1.2 | 1.2 |
| pH of wt/wt A + B mixture | 6.0 | 6.4 | 6.5 |
| Shades obtained: | matt very light blond | purple | red-purple |

EXAMPLE 7

| DYEING COMPOSITION | |
|---|---|
| 2,5-diaminonitrobenzene | 0.3 g |
| 4-hydroxy-5-ethoxyindole | 0.3 g |
| Para-phenylenediamine | 0.4 g |
| 1-methyl-2-hydroxy-4-aminobenzene | 0.1 g |
| Sodium lauryl ether sulphate containing 2 moles of ethylene oxide, sold as a formulation containing 28% of AS | 4.2 g AS |
| Oxyethylenated nonylphenol containing 9 moles of ethylene oxide | 1.0 g |
| Ethylene glycol monobutyl ether | 9.5 g |
| Monoethanolamine qs pH = 8.4 | |
| Sodium metabisulphite containing 35% of AS | 0.45 g AS |
| Sequestering agent qs | |
| Water qs | 100 g |

Weight for weight mixture with an oxidising composition: 20 volume hydrogen peroxide solution, the pH of which is adjusted to 1.3 using phosphoric acid.

Spontaneous pH of the mixture: 6.3.

This mixture is applied for 30 minutes to permanent-waved grey hair. After rinsing and shampooing, the hair is dyed red ash chestnut.

EXAMPLE 8

| DYEING COMPOSITION | |
|---|---|
| 4-hydroxy-5-methylindole | 0.45 g |
| 2,6-dimethyl-1,4-diamino-benzene.2 HCl | 0.64 g |
| Carrier 2 | |
| Monoethanolamine qs pH = 8.9 | |
| Water qs | 100 g |

OXIDISING COMPOSITION 20 volume hydrogen peroxide solution adjusted to pH 1.2 using phosphoric acid.

Grey hair which is 90% white is dyed by applying a weight for weight mixture of the dyeing composition and the oxidising composition. The pH of the mixture is 6.4. After leaving on the hair for 30 minutes, the hair is rinsed, washed with shampoo, rinsed again and then dried. The hair is dyed iridescent purple-violet.

| DYEING CARRIER 1 | |
|---|---|
| Nonylphenol containing 4 moles of ethylene oxide, sold under the name SINNOPAL NP4 by HENKEL | 25.5 g |

| DYEING CARRIER 1 | |
|---|---|
| Nonylphenol containing 9 moles of ethylene oxide, sold under the name SINNOPAL NP9 by HENKEL | 17.5 g |
| Ethylene glycol monoethyl ether | 7.0 g |
| Propylene glycol | 10.5 g |
| Dipropylene glycol | 0.5 g |
| Ethyl alcohol | 2.0 g |
| Monoethanolamine lauryl ether sulphate, sold under the name SACTIPON 2 OM 29 by LEVER as a formulation containing 28% of AS | 4.2 g AS |
| Sodium alkyl ether sulphate containing 28% of AS | 0.8 g AS |
| Aqueous sodium metabisulphite solution containing 35% of AS | 0.45 g AS |
| Sodium acetate | 0.8 g |
| Antioxidant, sequestering agent qs | |

| DYEING CARRIER 2 | |
|---|---|
| Polyglycerolated oleyl alcohol containing 2 moles of glycerol | 4.0 g |
| Polyglycerolated oleyl alcohol containing 4 moles of glycerol, containing 78% of AS | 5.69 g AS |
| Oleic acid | 3.0 g |
| Oleylamine containing 2 moles of ethylene oxide, sold under the name ETHOMEEN O 12 by AKZO | 7.0 g |
| Diethylaminopropyl laurylaminosuccinamate, sodium salt containing 55% of AS | 3.0 g AS |
| Oleyl alcohol | 5.0 g |
| Oleic acid diethanolamide | 12.0 g |
| Propylene glycol | 3.5 g |
| Ethyl alcohol | 7.0 g |
| Dipropylene glycol | 0.5 g |
| Propylene glycol monomethyl ether | 9.0 g |
| Aqueous sodium metabisulphite solution containing 35% of AS | 0.45 g AS |
| Ammonium acetate | 0.8 g |
| Antioxidant, sequestering agent qs | |

We claim:

1. A one-step method for dyeing keratinous fibres, wherein a composition containing, in a medium appropriate for dyeing, 0.01 to 3.5% by weight, relative to the total weight of the composition, of at least one coupler corresponding to the formula:

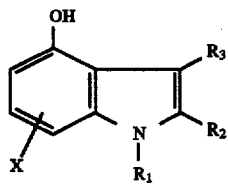

(I)

in which $R_1$ denotes a hydrogen atom or a $C_1$–$C_4$ alkyl radical; $R_2$ and $R_3$, which may be identical or different, denote a hydrogen atom, a $C_1$–$C_4$ alkyl radical, a carboxyl radical or an alkoxycarbonyl radical; and X denotes a hydrogen atom, a $C_1$–$C_4$ alkyl radical, a $C_1$–$C_{18}$ alkoxy radical, a halogen atom or an acetylamino group; at least one of the groups X, $R_1$, $R_2$ and $R_3$ being other than hydrogen; or salts of these compounds;

a tinctorially effective amount of at least one oxidation dye precursor; and at least one oxidizing agent selected from the group consisting of hydrogen peroxide, urea peroxide, persulfates, perborates and alkali metal bromates in a sufficient amount to oxidize the indole coupler and the oxidation dye precursor; is applied to said fibres, the pH of the composition applied to the fibres being less than 7 and said applied composition being free of iodide and nitrite ions in an amount sufficient to oxidize said indole coupler and said oxidation dye precursor.

2. Method according to claim 1, wherein
the compounds of formula (I) are chosen from the compounds in which the alkyl radical denotes methyl or ethyl and the alkoxycarbonyl radical denotes methoxycarbonyl or ethoxycarbonyl.

3. Method according to claim 1, in which the compounds of formula (I) are chosen from 4-hydroxy-5-methoxyindole, 4-hydroxy-2-ethoxycarbonyl-5-ethoxyindole, 4-hydroxy-2-methyl-5-ethoxyindole, 4-hydroxy-7-methoxy-2,3-dimethylindole, 4-hydroxy-5-methylindole, 4-hydroxy-5-ethoxyindole and 4-hydroxy-1-methyl-5-ethoxyindole.

4. Method according to claim 1, wherein the oxidation dye precursors are chosen from para-phenylenediamines, para-aminophenols and para heterocyclic precursors.

5. Method according to claim 4, wherein
the para-phenylenediamines are chosen from the compounds corresponding to the formula:

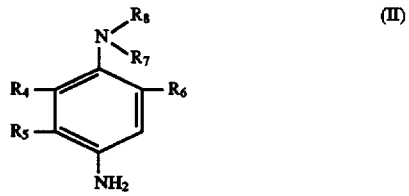

(II)

in which $R_4$, $R_5$ and $R_6$, which may be identical or different, represent a hydrogen or halogen atom, an alkyl radical having from 1 to 4 carbon atoms or an alkoxy radical having from 1 to 4 carbon atoms; and $R_7$ and $R_8$, which may be identical or different, represent a hydrogen atom or an alkyl, hydroxyalkyl, alkoxyalkyl, carbamylalkyl, mesylaminoalkyl, acetylaminoalkyl, ureidoalkyl, carbalkoxyaminoalkyl, piperidinoalkyl, or morpholinoalkyl radical in which the alkyl or alkoxy groups have from 1 to 4 carbon atoms, or $R_7$ and $R_8$ form, together with the nitrogen atom to which they are bonded, a piperidino or morpholino heterocycle, on condition that $R_4$ or $R_5$ represents a hydrogen atom when $R_7$ and $R_8$ do not represent a hydrogen atom, and the salts of these compounds.

6. Method according to claim 5, wherein the compounds of formula (II) are chosen from p-phenylenediamine, 2-methyl-p-phenylenediamine, methoxy-para-phenylenediamine, chloro-para-phenylenediamine, 2,6-dimethyl-para-phenylenediamine, 2,3-dimethyl-para-phenylenediamine, 2,5-dimethyl-para-phenylenediamine, 2-methyl-5-methoxy-para-phenylenediamine, 2,6-dimethyl-5-methoxy-para-phenylenediamine, N,N-dimethyl-para-phenylenediamine, 3-methyl-4-amino-N,N-diethylaniline, N,N-di-(β-hydroxyethyl)para-phenylenediamine, 3-methyl-4-amino-N,N-di-(β-hydroxyethyl)aniline, 3-chloro-4-amino-N,N-di-(β-hydroxyethyl)aniline, 4-amino-N,N-(ethyl, carbamylmethyl)aniline, 3-methyl-4-amino-N,N-(ethyl, carbamylmethyl)aniline, 4-amino-N,N-(ethyl,β-piperidino-ethyl)aniline, 3-methyl-4-amino-N,N-(ethyl,β-piperidino-ethyl)aniline, 4-amino-N,N-(ethyl,β-morpholinoethyl)-aniline, 3-methyl-4-amino-N,N-(ethyl,β-morpholinoethyl)-aniline, 4-amino-N,N-(ethyl,β-acetylaminoethyl)aniline, 4-amino-N-(β-methoxyethyl) aniline, 3-methyl-4-amino-N,N-(ethyl,β-acetylaminoethyl) aniline, 4-amino-N,N-(ethyl,β-mesylaminoethyl)aniline, 3-methyl-4-amino-N,N-(ethyl,β-mesylaminoethyl)aniline, 4-amino-N,N-(ethyl,β-sulpho-ethyl)aniline, 3-methyl-4-amino-N,N-(ethyl,β-sulpho-ethyl)aniline, N-[(4'-amino) phenyl]morpholine and N-[(4'-amino)phenyl]piperidine, in the form of the free base or of salts.

7. Method according to claim 4, wherein the p-aminophenols are chosen from p-aminophenol, 2-methyl-4-aminophenol, 3-methyl-4-aminophenol, 2-chloro-4-aminophenol, 3-chloro-4-aminophenol, 2,6-dimethyl-4-aminophenol, 3,5-dimethyl-4-aminophenol, 2,3-dimethyl-4-aminophenol, 2-hydroxymethyl-4-aminophenol, 2-(β-hydroxyethyl)-4-aminophenol, 2-methoxy-4-aminophenol, 3-methoxy-4-aminophenol, 2,5-dimethyl-4-aminophenol and 2-methoxymethyl-4-aminophenol.

8. Method according to claim 1, wherein the oxidation dye precursors are chosen from ortho-aminophenols and ortho-phenylenediamines.

9. Method according to claim 1, wherein the oxidising agent is chosen from hydrogen peroxide, urea peroxide, alkali metal bromates and persalts.

10. Method according to claim 1, wherein the pH of the composition applied to the keratinous fibres is between 3 and 6.9.

11. Method according to claim 1, in which the composition contains, in addition to the couplers of formula (I), other couplers chosen from meta-diphenols, meta-aminophenols, meta-phenylenediamines, meta-N-acylaminophenols, meta-ureidophenols, meta-carbalkoxyaminophenols, α-naphthol and couplers containing an active methylene group chosen from diketone compounds and pyrazolones.

12. Method according to claim 11, wherein the couplers are chosen from 2,4-dihydroxy-phenoxyethanol, 2,4-dihydroxyanisole, meta-aminophenol, resorcinol, resorcinol monomethyl ether, 2-methyl-resorcinol, pyrocatechol, 2-methyl-5-N-(β-hydroxy-ethyl)aminophenol, 2-methyl-5-N-(β-mesylaminoethyl)-aminophenol, 6-hydroxybenzomorpholine, 2,4-diaminoanisole, 2,4-diaminophenoxyethanol, 6-aminobenzomorpholine, [2-N-(β-hydroxyethyl)amino-4-amino]-phenoxyethanol, 2-amino-4-N-(β-hydroxyethyl)-aminoanisole, (2,4-diamino)phenyl-β,γ-dihydroxypropyl ether, 2,4-diaminophenoxyethylamine, 1,3-dimethoxy-2,4-diaminobenzene, 2-methyl-5-aminophenol, 2,6-dimethyl-3-aminophenol, 3,4-methylenedioxyphenol and 3,4-methylene-dioxyaniline and their salts.

13. Method according to claim 1, wherein the composition contains direct dyes, or mixtures thereof rapid oxidation dyes, or mixtures thereof.

14. Method according to claim 1, wherein the composition contains anionic, cationic, nonionic or amphoteric surface-active agents or mixtures thereof; thickeners, antioxidants, any other cosmetically acceptable adjuvant or mixtures thereof.

15. Method according to claim 1, wherein the medium appropriate for dyeing consists of water or a mixture of water and a solvent chosen from $C_2$–$C_4$ lower alkanols, glycerol, glycols, glycol ethers and aromatic alcohols or their mixtures.

16. Agent for dyeing keratinous fibres, which comprise at least two components: a component (A) consisting of a composition containing, in a medium appropriate for dyeing, 0.01 to 4% by weight, relative to the total weight of the component (A), of an indole coupler corresponding to the formula:

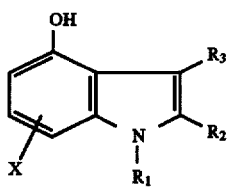

(I)

in which $R_1$ denotes a hydrogen atom or a $C_1$–$C_4$ alkyl radical; $R_2$ and $R_3$, which may be identical or different, denote a hydrogen atom, a $C_1$–$C_4$ alkyl radical, a carboxyl radical or an alkoxycarbonyl radical; and X denotes a hydrogen atom, a $C_1$–$C_4$ alkyl radical, a $C_1$–$C_{18}$ alkoxy radical, a halogen atom or an acetylamino group; at least one of the groups X, $R_1$, $R_2$ and $R_3$ being other than hydrogen; or salts of these compounds and 0.05 to 7% by weight, relative to the total weight of component (A), of an oxidation dye precursor, and a component (B) consisting of a composition containing an oxidizing agent selected from the group consisting of hydrogen peroxide, urea peroxide, persulfates, perborates and alkali metal bromates in a medium appropriate for dyeing, the pH of the components (A) and (B) being such that, after mixing in proportions of 90 to 10% in respect of component (A) and of 10 to 90% in respect of component (B), the resulting composition has a pH of less than 7, said resulting composition being free of iodide and nitrite ions in an amount sufficient to oxidize said indole coupler and said oxidation dye precursor.

17. Agent according to claim 16, in which the component (A) has a pH of between 3 and 10.5.

18. Agent according to claim 16, in which the component (A) contains surface-active agents in proportions of 0.1 to 55% by weight, solvents other than water in proportions of between 0.5 and 40% by weight, thickeners in proportions of between 0.1 and 5% by weight, antioxidants in proportions of between 0.02 and 1.5% by weight and any other cosmetically acceptable adjuvant, or their mixtures.

19. Agent according to claim 16, in which the component (B) has a pH which has a minimum value of 1 and is less than 7.

20. Method for dyeing keratinous fibres, which comprises a first step consisting in storing a dyeing agent as defined in claim 16 and, before application, in mixing the components (A) and (B) in proportions of 10 to 90% in respect of component (A) and of 90 to 10% in respect of component (B), so as to obtain a composition having a pH of less than 7, and applying this mixture immediately after preparation to the keratinous fibres.

21. Multi-compartment device or dyeing kit, which comprises at least two compartments, a first compartment of which contains the component (A) as defined in claim 16 and the second compartment of which contains the component (B) as defined in claim 16.

22. Device according to claim 21, which is fitted with means permitting a mixture of components (A) and (B) to be delivered onto the hair.

23. Dyeing method according to claim 1, wherein the composition is left on the hair for 3 to 40 minutes, the hair is rinsed, and shampooing is optionally carried out before rinsing again and drying.

* * * * *